United States Patent [19]

Goodall et al.

[11] Patent Number: 4,943,670

[45] Date of Patent: Jul. 24, 1990

[54] PREPARATION OF CONJUGATED DIENES

[75] Inventors: Brian L. Goodall, Akron, Ohio; Willem Terlouw; Jacob C. van der Sar, both of Amsterdam, Netherlands

[73] Assignee: Shell Oil Company, Houston, Tex.

[21] Appl. No.: 441,124

[22] Filed: Nov. 22, 1989

[51] Int. Cl.$^5$ .......................... C07C 2/76; C07C 1/20
[52] U.S. Cl. .................................. 585/601; 585/608
[58] Field of Search .................. 585/601, 608, 509

[56] References Cited

U.S. PATENT DOCUMENTS

| | | | |
|---|---|---|---|
| 4,180,694 | 12/1979 | Nozaki | 585/511 |
| 4,229,605 | 10/1980 | Nozaki | 585/509 |
| 4,229,606 | 10/1980 | Nozaki | 585/509 |
| 4,243,829 | 1/1981 | Pittman, Jr. et al. | 585/601 |
| 4,377,719 | 3/1983 | Pittman, Jr. et al. | 585/509 |
| 4,536,604 | 8/1985 | Lin et al. | 585/608 |
| 4,687,876 | 8/1987 | Nozaki | 585/509 |

FOREIGN PATENT DOCUMENTS

| | | |
|---|---|---|
| 4408 | 10/1979 | European Pat. Off. |
| 4409 | 10/1979 | European Pat. Off. |
| 4410 | 10/1979 | European Pat. Off. |
| 8139 | 2/1980 | European Pat. Off. |

*Primary Examiner*—Asok Pal
*Assistant Examiner*—J. Saba

[57] ABSTRACT

A process for the preparation of a compound of general formula

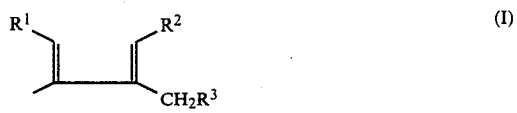

(I)

in which $R^1$ represents a hydrogen atom or a methyl group, one of $R^2$ and $R^3$ represents a hydrogen atom and the other of $R^2$ and $R^3$ is the same as $R^1$, which comprises reacting a compound of the general formula $$R^1CH=C=CH_2 \qquad (II)$$

with a salt of formic acid in the presence of a catalyst system comprising a palladium salt and a phosphorus compound of general formula $$P(OX)_n(X)_{3-n} \qquad (III)$$

in which n is 0,1,2 or 3 and each X independently represents an alkyl, alkenyl, aryl, aralkyl, alkaryl or cycloalkyl group, and recovering the desired compound of formula (I).

15 Claims, No Drawings

PREPARATION OF CONJUGATED DIENES

BACKGROUND OF THE INVENTION

This invention relates to the preparation of certain conjugated dienes. In a specific aspect, the invention relates to a process for preparing 2,3-dimethyl-butadiene, (E)-3-methyl-4-methylene-2-hexene and (E,E)-3,4-dimethyl-2,4-hexadiene.

Conjugated dienes are useful as monomers in the preparation of a wide variety of polymers such as elastomers and rubbers, and as chemical intermediates in the preparation of catalysts, pharmaceuticals and agrochemicals. Thus, for example, U.S. Pat. No. 4,532,301 describes the use of 2,3-dimethylbutadiene in the preparation of radial block polymer polymerization initiators.

In the preparation of such alkyl-substituted conjugated dienes, the product is often a mixture of the desired product with polymers and isomers thereof. This results in lower yields.

It is therefore an object of the invention to provide a process for preparing certain alkyl-substituted conjugated dienes in high yield and good conversion. It is another object of the invention to provide a cost effective and convenient process for preparing the alkyl-substituted conjugated dienes.

BRIEF SUMMARY OF THE INVENTION

Preparation of Conjugated Dienes

A process for the preparation of a compound of general formula

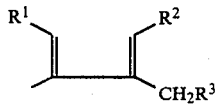

in which $R^1$ represents a hydrogen atom or a methyl group, one of $R^2$ and $R^3$ represents a hydrogen atom and the other of $R^2$ and $R^3$ is the same as $R^1$, which comprises reacting a compound of general formula $$R^1CH=C=CH_2 \quad (II)$$

with a salt of formic acid in the presence of a catalyst system comprising a palladium salt and a phosphorus comound of general formula $$P(OX)_n(X)_{3-n} \quad (III)$$

in which n is 0, 1, 2, or 3 and each X independently represents an alkyl, alkenyl, aryl, aralkyl, alkaryl or cycloalkyl group, and recovering the desired compound of formula (I).

Detailed Description of the Invention

It has now been found that 2,3-dimethyl-butadiene, (E)-3-methyl-4-methylene-2-hexene and (E,E)-3,4-dimethyl-2,4-hexadiene can be prepared by hydrodimerising propadiene or 1,2-butadiene. Accordingly, the present invention provides a process for the preparation of a compound of general formula

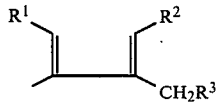

in which $R^1$ represents a hydrogen atom or a methyl group, one of $R^2$ and $R^3$ represents a hydrogen atom and the other of $R^2$ and $R^3$ is the same as $R^1$, which comprises reacting a compound of general formula $$R^1CH=C=CH_2 \quad (II)$$

with a salt of formic acid in the presence of a catalyst system comprising a palladium salt and a phosphorus compound of general formula $$P(OX)_n(X)_{3-n} \quad (III)$$

in which n is 0, 1, 2, or 3 and each X independently represents an alkyl, alkenyl, aryl, aralkyl, alkaryl or cycloalkyl group, and recovering the desired compound of formula (I).

In the invention process, the salt of formic acid may optionally be generated in situ by reacting formic acid with an appropriate base. When the salt of formic acid is generated in situ, the amount of base used should be at least sufficient to neutralize the formic acid present in the reactor. The formic acid may be added at the start of the reaction and/or continuously or stepwise during the reaction. An advantage of adding the formic acid continuously or stepwise is that less base is required. Also, continuous addition of formic acid in the hydrodimerisation of 1,2-butadiene appears to increase the selectivity of the reaction in favor of (E)-3-methyl-4-methyl-2-hexene.

Preferred salts of formic acid are alkali metal salts, for example those formed by reaction with alkali metal hydroxides or carbonates such as sodium or potassium hydroxide or carbonate, and salts of tertiary organic amines, for example triethylamine.

The palladium salt employed in the invention process is conveniently a palladium carboxylate, nitrate or halide. Palladium acetate is particularly preferred.

The molar ratio of the compound of formula (II) to palladium salt is not critical, and will be determined primarily by economic and practical considerations. It is preferably not more than 50,000.

Referring to the phosphorus compound of general formula (III), any alkyl or alkenyl group present preferably has from 1 to 20, more preferably from 3 to 10 carbon atoms. Preferably any branching occurs at a carbon atom no more than two carbon atoms from the phosphorus atom, as for example in an isopropyl group. An aryl group is preferably a phenyl group. An aralkyl group is preferably a benzyl group. An alkaryl group is preferably a ditertiarybutyl phenyl group or an ortho-tolyl group. A cycloalkyl group preferably has from 3 to 6 carbon atoms.

Particularly preferred phosphorus compounds of general formula (III) are triphenylphosphine, tri-isopropylphosphine, diphenylisopropylphosphine, tribenzylphosphine, tri(ortho-toluyl)phosphine and tri(2,4-ditertiarybutylphenyl)phosphite. Optionally more than one phosphorus compound may be employed. For example a mixture of triphenylphosphine and tri-(2,4-ditertiarybutyl-phenyl)phosphite may be used. The use of tri-isopropylphosphine alone is most preferred.

The molar ratio of phosphorus compound of general formula (III) to palladium salt is conveniently in the range of from about 1:1 to 20:1, preferably about 1.5:1 to 4:1.

The invention process is conveniently carried out at temperatures in the range of from about 30° to 100° C., preferably from about 40° to 70° C.

Although a solvent is not essential in the invention process, the reaction is preferably performed in the presence of a solvent. Suitable solvents include amides such as dimethylformamide or dimethylacetamide; tertiary amines such as triethylamine or pyridine; aromatic hydrocarbons such as benzene, toluene or the three xylenes; sulphoxides such as dimethylsulphoxide; ethers such as tetrahydroduran; nitriles such as benzonitrile; nitro compounds such as nitromethane or nitrobenzene; halogenated hydrocarbons such as chlorobenzene and chloroform; and carbonates such as propylene carbonate. Preferably the reaction is performed in the presence of a polar aprotic solvent.

The process is conveniently carried out at a pressure in the range of from 2 to 25 bar, most preferably under autogenic pressure.

The compounds of general formula (I) may be recovered from the reaction mixture using conventional techniques such as distillation. Thus as described in J. Am. Chem. Soc., Vol. 110, No. 6, 1988, 1883–1889, has a boiling point of 127° C. at 760 mm Hg, and (E,E)-3,4-dimethyl-2,4-hexadiene has a boiling point of 134.5° C. at 760 mm Hg.

The invention process affords the compounds of general formula (I) in high yield with good conversion, without the production of substantial quantities of polymeric materials and isomers of the compounds of formula (I). It is also advantageous because propadiene and, in particular, 1,2-butadiene are inexpensive and readily available.

The following Examples illustrate specific embodiments of the invention process.

EXAMPLE 1

Preparation of 2,3-dimethylbutadiene

A 250 ml stainless steel reactor (under nitrogen) was loaded with dimethylformamide (40 ml) and a catalyst solution (additional 10 ml of dimethylformamide) consisting of palladium acetate (0.1 mmol) and triisopropylphosphine (0.2 mmol). To this homogeneous system a mixture of triethylamine (0.4 mol) and formic acid (0.4 mol) was added. Finally propadiene (1 mol, 25% excess) was added and the temperature was raised from 20° C. to 40° C. After 24 hours, the conversion based on formic acid was 100%, and only 2,3-dimethylbutadiene was obtained as the product.

EXAMPLE 2

Preparation of 2,3-dimethylbutadiene

The method of Example 1 was repeated except triphenylphosphine was used instead of triisopropylphosphine, and the temperature was raised to 43° C. and the duration of the reaction was 21 hours. Conversion was 100% based on formic acid with selectivity.

EXAMPLE 3

Preparation of (E)-3-methyl-4-methylene-2-hexene and (E,E)-3,4-dimethyl-2,4-hexadiene In a 250 ml stainless steel reactor (under nitrogen), formic acid (9.2 g, 0.2 mol) triethylamine (20.2 g, 0.2 mol) palladium acetate (22 mg, 0.1 mmol), triphenylphosphine (60 mg, 0.2 mmol) and 1,2-butadiene (22 g, 0.4 mol) were added to dimethylformamide (100 ml). The reaction mixture was heated to 50° C. with stirring for 2.5 hours, after which time the reaction was stopped. Conversion was based on formic acid with the following product distribution: (E)-3-methyl-4-methylene-2-hexene (65%); (E,E)-3,4-dimethyl-2,4-hexadiene (27%) and 1,7-octadiene (8%). The products were readily separated by distillation.

EXAMPLE 4

Preparation of (E)-3-methyl-4-methylene-2-hexene and (E,E)-3,4-dimethyl-2,4-hexadiene The method of Example 3 was repeated, except triisopropylphosphine was used instead of triphenylphosphine, and the reaction mixture was heated to 60° C. and stopped after 22 hours. Conversion was 50% based on formic acid with the following product distribution: (E)-3-methyl-4-methylene-2-hexene (47%); (E,E)-3,4-dimethyl-2,4-hexadiene (46%) and 1,7-octadiene (7%).

EXAMPLES 5 TO 14

Ten further experiments were performed using 1,2-butadiene as the substrate following methods analogous to those described in Examples 1 to 4. In each case the palladium salt was palladium acetate. In Examples 5 to 13 the solvent was dimethylformamide (DMF), while in Example 14 it was propylene carbonate. As with Examples 1 to 4, the pressure was autogenic (typically starting at 3 bar and rising to about 7 bar during the reaction). The base and formic acid were always mixed together in the solvent prior to the addition of the catalyst components (phosphorus compound and palladium acetate dissolved in a solvent) and 1,2-butadiene.

The amounts of reactants, the reaction conditions and the results are summarized in the Table. In each case, the percent conversion is based on formic acid.

EXAMPLE 15

A 6 l stainless steel reactor (under nitrogen) was loaded with dimethyl formamide (1000 ml), triethylamine (4 mol), formic acid (3,8 mol), a clear solution of palladium acetate (1 mmol), tri-isopropylphosphine (1.9 mmol) in 50 ml additional dimethylformamide, and 1,2-butadiene (8.3 mol). The reaction mixture was heated to 43°–48° C. with stirring for 25 hours until completion. The product distribution was: (E)-3-methyl-4-methylene-2-hexene (53%), (E,E)-3,4-dimethyl-2,4-hexadiene (27%) and 1,7-octadiene (6%).

EXAMPLE 16

A 6 l stainless steel reactor (under nitrogen) was loaded with a clear solution of palladium acetate (3.0 mmol), tri-isopropylphosphine (6.0 mmol), triethylamine (3.0 mol) and 1,2-butadiene (15.6 mol). One portion of formic acid (1.5 mol) was added to the reactor while heating the reactor to 40°–45° C. After three hours reaction time, formic acid (6 mol) was added continuously over 11 hours with stirring. The reaction was allowed to complete in an additional 10 hours. The product distribution was: (E)-3-methyl-4-methylene-2-hexene (76%); (E,E)-3,4-dimethyl-2,4-hexadiene (19%) and 1,7-octadiene (4%).

TABLE

| Ex. No. | 1,2-butadiene mol | formic acid mol | base mol | Pd (OAc)$_2$ mmol | Phosphorus compound mmol | Solvent | Temp °C. | Time hours | Conversion % | Selectivity *MMH % w | *DMHXD % w | *OD % w |
|---|---|---|---|---|---|---|---|---|---|---|---|---|
| 5 | 0.22 | 0.1 | KOH 0.1 | 0.1 | P(iPR)$_3$ 0.2 | 100 ml | 70 | 18 | 40 | 53 | 37 | 10 |
| 6 | 0.4 | 0.2 | KOH 0.2 | 0.1 | PPh$_3$ 0.3 | 100 ml | 50 | 12 | 28 | 65 | 28 | 7 |
| 7 | 0.4 | 0.2 | Et$_3$N 0.2 | 0.1 | PPh$_3$ 3.6 | 100 ml | 95 | 0.5 | 72 | 64 | 28 | 8 |
| 8 | 0.4 | 0.2 | Na$_2$CO$_3$ 0.1 | 0.1 | DTBP 0.3 | 100 ml | 50 | 48 | 22 | 45 | 34 | 21 |
| 9 | 0.4 | 0.2 | Et$_3$N 0.2 | 0.1 | DTPB 1.0 | 100 ml | 50 | 6 | 25 | 60 | 33 | 7 |
| 10 | 0.4 | 0.2 | Et$_3$N 0.2 | 0.1 | DTBP 0.2 + PPh$_3$ 0.1 | 100 ml | 50 | 6 | 93 | 60 | 33 | 7 |
| 11 | 0.8 | 0.38 | Et$_3$N 0.4 | 0.1 | PPh$_3$ 0.2 | 100 ml | 42 | 21 | 100 | 67 | 27 | 6 |
| 12 | 1.2 | 0.38 | Et$_3$N 0.4 | 0.1 | PPh$_2$(iPr) 0.2 | 100 ml | 42 | 20 | 100 | 71 | 25 | 4 |
| 13 | 1.0 | 0.38 | Et$_3$N 0.4 | 0.1 | P(i-Pr)$_3$ 0.2 | 100 ml | 42 | 20 | 97 | 55 | 41 | 4 |
| 14 | 0.8 | 0.38 | Et$_3$N | 0.1 | PPh$_3$ | 114 g | 42 | 20 | 100 | 60 | 35 | 5 |

MMH: (E)-3-methyl-4-methylene-2-hexene
DMHXD: (E,E)-3,4-dimethyl-2,4-hexadiene
OD: 1,7-octadiene
iPr: isopropyl
Ph: phenyl
DTPB: 2,4-di-tertiarybutylphenyl phosphite

We claim:

1. A process for the preparation of a compound of general formula

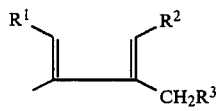  (I)

in which $R^1$ represents a hydrogen atom or a methyl group, one of $R^2$ and $R^3$ represents a hydrogen atom and the other of $R^2$ and $R^3$ is the same as $R^1$, which process comprises reacting a compound of general formula

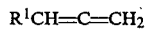  (II)

with a salt of formic acid in the presence of a catalyst system comprising a palladium salt and a phosphorus compound of general formula

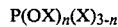  (III)

in which n is 0, 1, 2, or 3 and each X independently represents an alkyl, alkenyl, aryl, aralkyl, alkaryl or cycloalkyl group, and recovering the desired compound of formula (I).

2. The process of claim 1 in which the salt of formic acid is an alkali metal salt.

3. The process of claim 1 in which the salt of formic acid is a tertiary organic amine.

4. The process of claim 3 in which the salt of formic acid is a triethylamine salt.

5. The process of claim 1 in which the palladium salt is selected from carboxylates, nitrates and halides.

6. The process of claim 5 in which the palladium salt is palladium acetate.

7. The process of claim 1 in which X is selected from alkyl or alkenyl groups having from 3 to 10 carbon atoms, phenyl groups, di-tertiarybutylphenyl groups and cycloalkyl groups having from 3 to 6 carbon atoms.

8. The process of claim 7 in which the phosphorus compound of general formula (III) is selected from triphenylphosphine, tri-isopropylphosphine, diphenylisopropylphosphine, tribenzylphosphine, tri(orthotoluyl)phosphine and tri-(2,4-di-tertiarybutylphenyl)phosphite.

9. The process of claim 8 in which the phosphorus compound of general formula (III) is tri-isopropylphosphine.

10. The process of claim 1 in the molar ratio of phosphorus compound of general formula (III) to palladium salt is within the range of from about 1:1 to 20:1.

11. The process of claim 1 in which the reaction temperature is within the range of from about 30° to 100° C.

12. The process of claim 1 in which the reaction is performed in the presence of a solvent selected from dimethylformamide, dimethylacetamide, pyridine, triethylamine, dimethylsulphoxide, tetrahydrofuran, benzonitrile, nitromethane, nitrobenzene and propylene carbonate.

13. The process of claim 1 in which the reaction pressure is in the range of from about 2 to 25 bar.

14. The process of claim 13 in which the pressure is autogenic.

15. The process of claim 1 in which the salt of formic acid is a triethylamine; the palladium salt is palladium acetate; and the phosphorus compound of the general formula (III) is selected from triphenylphosphine, triisopropylphosphine and the mixtures thereof.

* * * * *